(12) United States Patent
Healy

(10) Patent No.: US 10,239,078 B2
(45) Date of Patent: Mar. 26, 2019

(54) POWDERED SCENT COMPOUND

(71) Applicant: Windage, LLC, Rochester, MN (US)

(72) Inventor: David Healy, Orono, MN (US)

(73) Assignee: WINDAGE, LLC, Rochester, MN (US)

( * ) Notice: Subject to any disclaimer, the term of this patent is extended or adjusted under 35 U.S.C. 154(b) by 41 days.

(21) Appl. No.: 15/292,459

(22) Filed: Oct. 13, 2016

(65) Prior Publication Data

US 2017/0099839 A1 Apr. 13, 2017

Related U.S. Application Data

(60) Provisional application No. 62/240,911, filed on Oct. 13, 2015.

(51) Int. Cl.
| | |
|---|---|
| *B05B 11/00* | (2006.01) |
| *B05B 11/04* | (2006.01) |
| *A01M 9/00* | (2006.01) |
| *A01M 31/00* | (2006.01) |
| *A61L 9/012* | (2006.01) |
| *A61L 9/14* | (2006.01) |

(52) U.S. Cl.
CPC .............. *B05B 11/041* (2013.01); *A01M 9/00* (2013.01); *A01M 31/008* (2013.01); *A61L 9/012* (2013.01); *A61L 9/14* (2013.01); *A61L 2209/134* (2013.01); *A61L 2209/15* (2013.01)

(58) Field of Classification Search
CPC ...... A01M 9/00; A01M 31/008; B05B 11/041
See application file for complete search history.

(56) References Cited

U.S. PATENT DOCUMENTS

| | | | | |
|---|---|---|---|---|
| 4,536,315 | A | * 8/1985 | Ramachandran | ...... C11D 3/126 510/349 |
| 5,840,668 | A | * 11/1998 | Behan | .................... C11D 3/505 510/112 |
| 2006/0016905 | A1 | * 1/2006 | Roreger | .............. A01M 1/2055 239/34 |
| 2012/0090557 | A1 | * 4/2012 | Slade, Jr. | ............... A01K 15/02 119/712 |

* cited by examiner

*Primary Examiner* — Arrie L Reuther
(74) *Attorney, Agent, or Firm* — McAndrews, Held & Malloy, Ltd.

(57) ABSTRACT

A powdered scent compound and related methods of application for adhering the powdered scent compound to a desired application area. The powdered scent compound can comprise a porous carrier powder, an adhesive compound and a synthetic scent compound. The powdered scent compound is shelf-stable and convenient to apply, carry and store. Furthermore, the powdered scent compound can adhere to applied surfaces, thereby ensuring that powdered scent compound remains where it is applied, even in locations where the potential exists for the compound to drip or be blown from.

8 Claims, 3 Drawing Sheets

US 10,239,078 B2

POWDERED SCENT COMPOUND

RELATED APPLICATION

The present application claims the benefit of U.S. Provisional Application No. 62/240,911 filed Oct. 13, 2015 and entitled "POWDERED SCENT COMPOUND", which is hereby incorporated in its entirety by reference.

FIELD OF THE INVENTION

The present invention is generally directed to the field of scent dispersal in the outdoors. More specifically, the present invention is directed to a powdered scent compound with adhesive properties for airborne dispensing onto desired surfaces for the attraction of wildlife.

BACKGROUND OF THE INVENTION

Scents are widely used in the outdoors industry and especially related to the hunting of large game. Typically, these scents are used for the purpose of attracting wild game such as, for example, whitetail deer, or to mask or otherwise reduce human odor so as to make a hunter harder for an animal to detect.

Representative scent products that are readily available from outdoor retailers include liquids made from natural doe urine and glandular secretions harvested from living deer. Suppliers of these liquid scent products include companies such as Tinks and Hunter Specialties. These scent products are typically packaged in glass or plastic bottles and can be cumbersome and messy when carried into the field and can be difficult to apply in certain desirable locations. Furthermore, the natural elements utilized in these liquid scents undergo instant changes at the molecular level when harvested and/or packaged for retail sales. These changes can include the breakdown of urine into ammonia and other byproducts that can reduce their effectiveness in the field. In addition, these liquid products possess a limited shelf life and are usually discarded after the relevant season.

Another representative product uses natural doe urine but then freeze dries the urine into a powdered form. While this freeze dried product can avoid the messiness and shelf life issues associated with conventional liquid products, prior to freeze drying, the natural doe urine similarly undergo natural molecular changes instantly upon collection that can reduce the effectiveness of the freeze dried powder.

Another downside with use of natural doe urine, either in liquid or powdered form, is the concern regarding the potential transmission of diseases and other maladies. For example, various locations have begun considering banning the use of natural doe urine to prevent the transmission of Chronic Wasting Disease (CWD) in the whitetail deer herd.

While there presently exist a number of scent-based products for the outdoors and hunting industry, there remains a need for additional effective measures that allow for combining elements and scent compounds for scent dispersal.

SUMMARY OF THE INVENTION

Generally, a powdered scent compound according to embodiments of the present invention address the aforementioned needs by providing a synthetic, shelf-stable compound that is convenient to apply, carry and store. Furthermore, the powdered scent compound of the present invention can adhere to applied surfaces, thereby ensuring that compound remains where it is applied, even in locations where the potential exists for the compound to drip from or be blown from. Due to the adhesive nature of the powdered scent compound, the compound can be applied to or can simulate locations such as, for example, deer scrapes on overhead licking branches or on lower branches, brush or dirt while remaining adhered in the applied location. Once applied and adhered to a desired location, the powdered scent compound can be rehydrated through exposure to precipitation such as rain or snow, thus allowing the compound to actively distribute scent for extended periods of time.

Representative embodiments of a powdered scent compound of the present invention can comprise a porous carrier or binder component, an adhesive component and a synthetic scent component. The carrier or binder component can comprise from about 50 to about 95% by weight of the powdered scent compound. In one representative embodiment, the carrier or binder component comprises talc or talcum powder. The adhesive component can comprise from about 5 to about 50% by weight of the powdered scent compound. In one representative embodiment, the adhesive component comprise sodium carbonate and/or hydrogenated silica. The synthetic scent compound can comprise from about 1 to about 5% by weight of the powdered scent compound. In one representative embodiment, the synthetic scent compound can comprise about 50 percent or more by weight dioctyl adipate, about 10 percent to about 25 percent by weight ethyl laurate; about 5 percent to about 10 percent by weight benzyl benzoate and/or musk xylol and about 1 percent to about 5 percent ethyl decanoate, p-cresol, p-cresyl phenylacetate, and/or phenyl acetic acid. In some embodiments, the synthetic scent compound can further include about 1 percent or less by weight of an ingredient selected from the group consisting of: benzyl alcohol, benzyl phenyl acetate, coumarin crystals, cuminic aldehyde, ethy-2-hexanol, ethylphenyl acetate, geranyl acetate, isovaleric acid, and patchouli oil. In some embodiments, the synthetic scent compound is formulated to simulate gland secretions or urine from either male or female deer. In some embodiments, the powdered scent compound is shelf-stable and has a shelf-life of at least one year such that the powdered scent compound is effective for multiple hunting seasons.

In representative embodiments of the present invention, a powdered scent compound can be formulated for air borne dispersal onto a desired surface. In some embodiments, the powdered scent compound can be contained within a container including a cap for covering a container opening. After removing the cap, the container can be squeezed resulting in a portion of the powdered scent compound exiting the container opening in a spray of powder that is directed into a desired area, for example, on or around trees and brush. In some embodiments, the desired application area can comprise an overhead branch for example, on or simulating a licking branch of a male deer. The powdered scent compound remains attached and adhered to the desired area due to the presence of an adhesive component within the powdered scent compound. The adhered powdered scent compound functions to attract wild game and cover human odor scents. In some embodiments, the cap can comprise a flip-style lid capable of being rotated between the open position and a closed position. The container can also include an attachment member operably connected to a receiving member on the container, the attachment member allowing the container to be retained on a holding item.

In some representative embodiments, a powdered scent compound can be manufactured by adding a porous carrier or binder component and an adhesive component into a mixer. The porous carrier and adhesive component can then be mixed within the mixer. As the porous carrier and adhesive component are mixed, a synthetic scent compound can be sprayed into the mixer whereby the synthetic scent compound is absorbed into the porous carrier to form a bulk powdered scent compound. The bulk powdered scent compound can then be directed through a screen assembly such that the bulk powdered scent is broken into a fine powder for packaging within a dispenser. In some embodiments, a desiccant can be added to the dispenser to absorb any excess moisture so as to prevent clumping of the fine powder.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
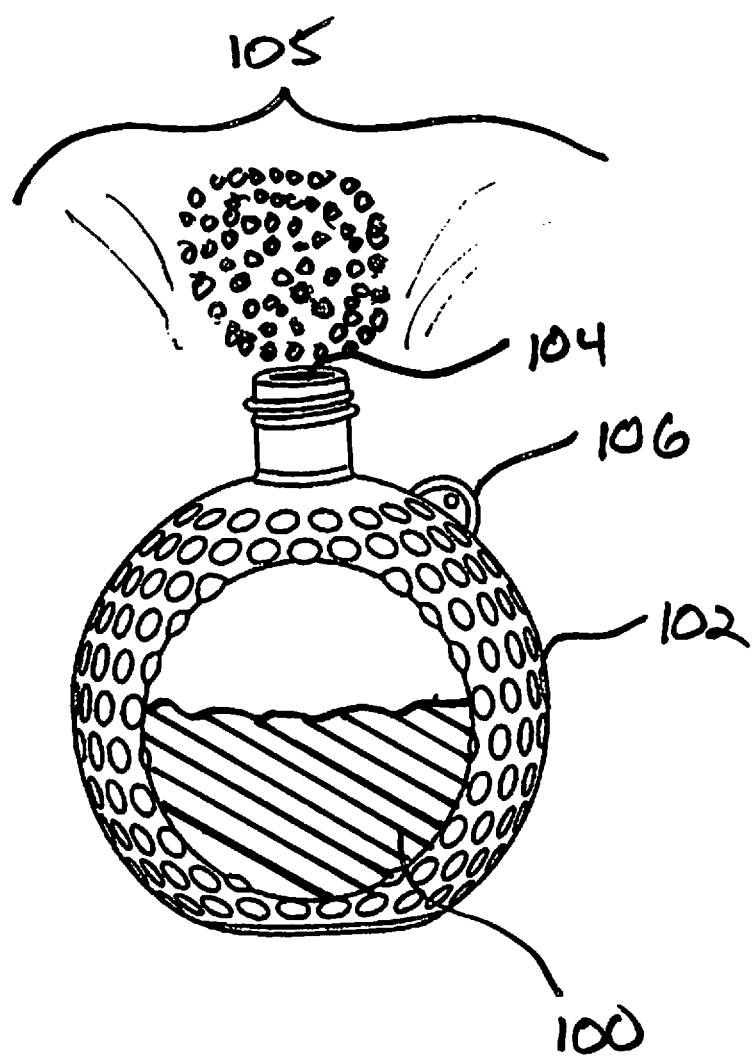
FIG. 1 is a perspective view an embodiment of a container being used to spray a powdered scent compound of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

We have found that there are profound advantages in using the presently disclosed powdered scent compound for the attraction of wildlife and/or the covering of human scent. Generally, the powdered scent compound is advantageous in that a powdered form is easy to apply, an adhesive component maintains the powdered scent compound in a desired application area and a synthetic scent compound is shelf-stable and remains effective for at least one year, thereby providing for use during multiple hunting seasons.

The present invention is advantageous and unique because it can combine natural and synthetic oil based scent compounds with a porous carrier, for example, talcum powder along with an adhesive compound to transform the delivery mechanism to a very lightweight powder form that adheres to an application point. The powdered scent compound can be dispensed via a spray bottle, for example, the design illustrated in U.S. Design application Ser. No. 29/255,577 and as illustrated in FIG. 1, whereby the sprayed powder can become airborne, be applied and adhered directly to clothing or onto soil, trees or other vegetation. The powdered scent system generally comprises a squeezable container that holds a quantity of the powdered scent compound. By quickly squeezing and releasing the container, a quantity of the powdered scent compound is dispelled through an opening portion in the cap into the surrounding air where it disperses scent for the purpose of attracting wild game and reducing human odor. In some embodiments, the powdered scent system can further include a desiccant placed within the container, whereby the desiccant is adapted to remain within the container as the powdered scent compound is dispensed.

With reference to FIG. 1, one aspect of the present invention is directed to a method for using a powdered scent compound 100. Generally, the method can comprise mixing the powdered scent compound 100 so as to include a porous carrier powder, an adhesive compounds and a synthetic scent compound. The method can further comprise filling a container 102 with an amount of the powdered scent compound 100. The method can further comprise applying the powdered scent compound 100 to a desired application area by squeezing the container 102 to quickly eject the powdered scent compound 100 through an opening portion 104 in the container 102 such that the powdered scent compound 100 interacts with an application area 105, for example, the surrounding air, foliage and/or soil, to provide both wild game attraction and human odor control. In some embodiments, the container can include an attachment member 106 allowing a user to carry the container by attaching it to an article of clothing.

A representative embodiment of a powdered scent compound of the present invention can comprise a formulation of a porous carrier powder, an adhesive compound and a synthetic scent compound. The porous carrier or binder powder comprises a suitable powdered material that is preferably biodegradeable or otherwise environmentally friendly. In some embodiments, the porous carrier or binder powder can comprises talc or talcum powder. The adhesive component is also preferably formed of a biodegradable or environmentally friendly material. In some embodiments, the adhesive component can comprise sodium carbonate and/or hydrogenated silica. The synthetic scent compound is also preferably formed of a biodegradable or environmentally friendly material. In some embodiments, synthetic scent compound can comprise about 50 percent or more by weight dioctyl adipate, about 10 percent to about 25 percent by weight ethyl laurate; about 5 percent to about 10 percent by weight benzyl benzoate and/or musk xylol and about 1 percent to about 5 percent ethyl decanoate, p-cresol, p-cresyl phenylacetate, and/or phenyl acetic acid. In some embodiments, the synthetic scent compound can further include about 1 percent or less by weight of an ingredient selected from the group consisting of: benzyl alcohol, benzyl phenyl acetate, coumarin crystals, cuminic aldehyde, ethy-2-hexanol, ethylphenyl acetate, geranyl acetate, isovaleric acid, and patchouli oil. In some embodiments, the powdered scent compound is shelf-stable and has a shelf-life of at least one year such that the powdered scent compound is effective for multiple hunting seasons. Generally, embodiments of the powdered scent compound can be formulated as contained in Table 1 below:

TABLE 1

Representative Formulation of Powdered Scent Compound

| Component | Weight Percent |
|---|---|
| Porous Carrier or Binder Powder | 50-95 |
| Adhesive Compound | 5-50 |
| Synthetic Scent Compound | 1-5 |

Figure 2:
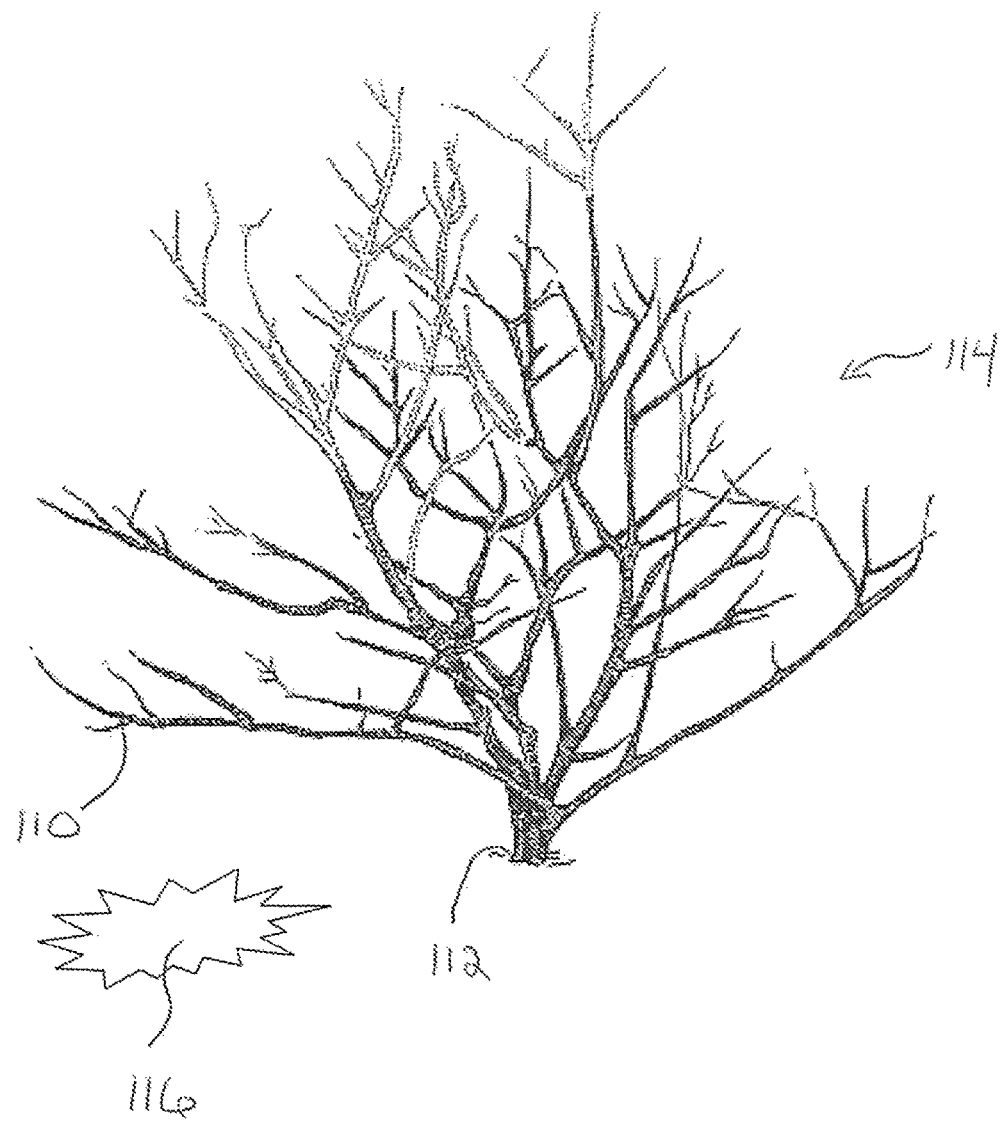
FIG. 2 is a side view of a tree illustrating representative application areas for a powdered scent compound of the present invention.

As illustrated in FIG. 2, one use of the powdered scent compound 100 of the present invention can be directed to application onto or the simulation of deer scrapes either prior to or during the rut. For instance, powdered scent compound 100 can sprayed onto an overhead "licking" branch 110 that can be located anywhere from 3 to 6 feet above the ground. The adhesive compound serves to adhere the powdered scent compound 100 on the licking branch 110 for extended period times as opposed to liquid running, dripping or being blown off of the licking branch 110. When the powdered scent compound 100 is applied to the licking branch, the synthetic scent compound is preferably formulated to simulate glandular secretions from the pre-orbital gland of a male deer. Alternatively, powdered scent compound 100 can be applied and adhered directly onto or to simulate deer scrapes on a lower portion 112 or base of a tree 114 or directly onto a patch of ground 116. When applied to the lower portion 112 or ground 116, the synthetic scent compound can be formulated to simulate either glandular secretions or urine, from either male or female deer. When adhered to the licking branch 110, the lower portion 112 and/or ground 116, exposure of the powdered scent compound 100 to precipitation including, for example, snow or rain can rehydrate the synthetic scent compound such that the desired scent is released again, thereby extending the life of the applied powdered scent compound 100.

Figure 3:
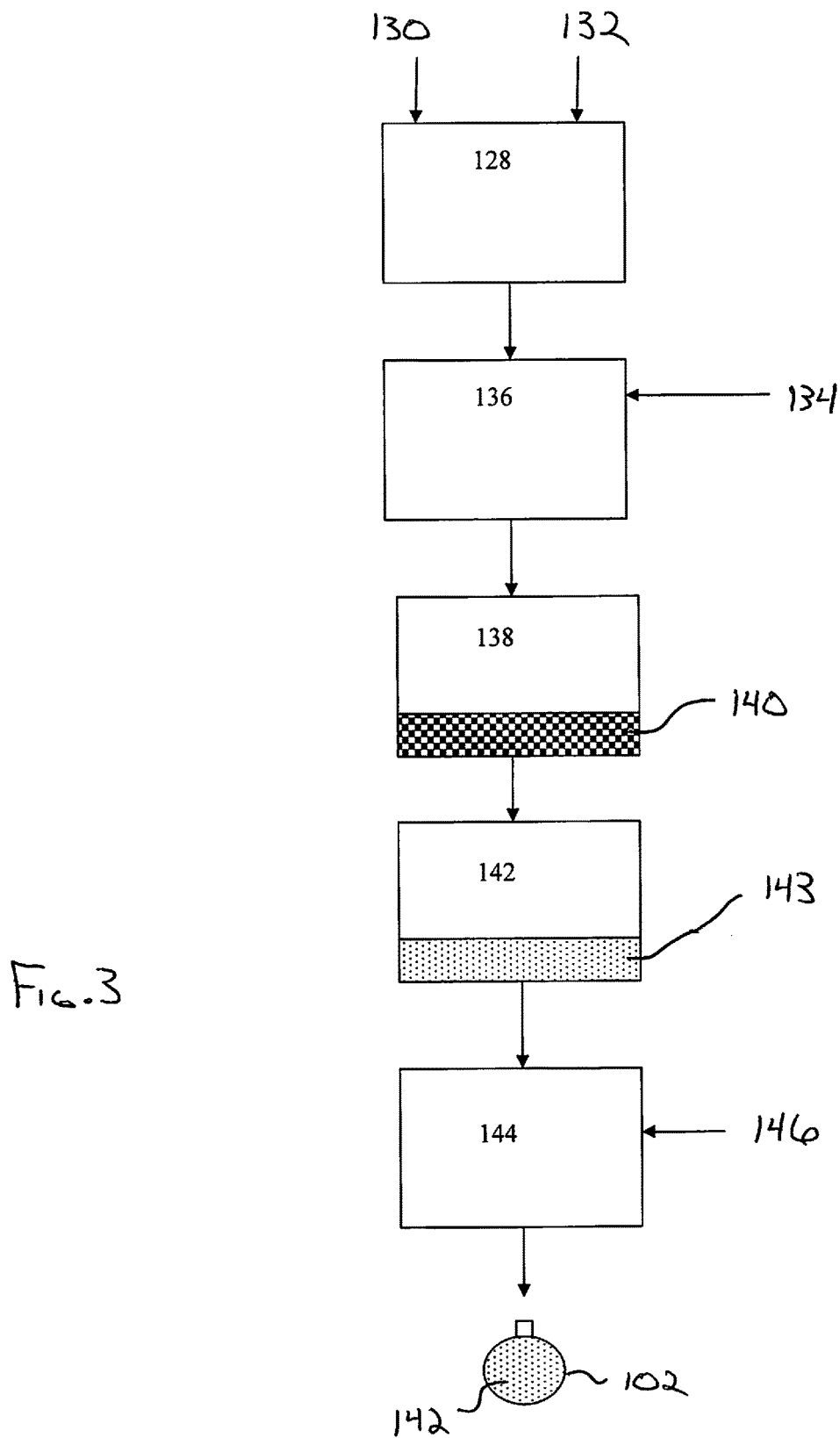
FIG. 3 is a flowchart illustrating a representative method for preparing a powdered scent compound of the present invention.

Referring to FIG. 3, a representative process for manufacturing the powdered scent compound 100 can comprise a first mixing step 128 wherein a porous carrier/binder component 130 and an adhesive component 132 are each added into a conventional mixer. With the porous carrier 130 and adhesive component 132 mixed together, a synthetic scent compound 134 can be sprayed into the mixer in a spraying step 136. As the synthetic scent compound 134 is sprayed, the mixer mixes the synthetic scent compound 134 into the porous carrier 130 and adhesive component 132 in a second mixing step 138 so as to form a bulk powdered scent compound 140 in which the synthetic scent compound 134 has been absorbed into the porous carrier 130. In a screening step 142, the bulk powdered scent compound 140 is forced through a screen so as break any large chunks or agglomerations of bulk powdered scent compound 140 into a fine powder 143 of powdered scent compound 100. In a packaging step 144, the container 102 can be filled with the fine powder 143, whereby the powdered scent compound 100 is prepared for dispensing. In some embodiments, a desiccant 146 can be added as part of packaging step 144 to absorb any excess moisture and to prevent clumping of the fine powder 143 within the container 102. Desiccant 146 can comprise materials such as, for example, silica gel or even grains of rice, that are either large enough or otherwise packaged in porous packets, such that the desiccant 146 is not expelled when applying the powdered scent compound 100 by squeezing the container 102.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A powdered scent compound for attracting wildlife, comprising:
a porous carrier in a powder form;
an adhesive compound; and
a synthetic scent compound absorbed into the porous carrier,
wherein the powdered scent compound comprises, from about 1 to about 5 percent by weight of the powdered scent compound, the synthetic scent compound, and
wherein the synthetic scent compound comprises
about 50 percent or more by weight of the synthetic scent compound, dioctyl adipate,
about 10 percent to about 25 percent by weight of the synthetic scent compound, ethyl laurate;
about 5 percent to about 10 percent by weight of the synthetic scent compound, one or both of benzyl benzoate and musk xylol, and
about 1 percent to about 5 percent by weight of the synthetic scent compound, one or more of ethyl decanoate, p-cresol, p-cresyl phenylacetate, and phenyl acetic acid.

2. The powdered scent compound of claim 1, wherein the porous carrier comprises from about 50 to about 95 percent by weight of the powdered scent compound.

3. The powdered scent compound of claim 2, wherein the porous carrier powder comprises talcum powder.

4. The powdered scent compound of claim 1, wherein the adhesive compound comprises from about 5 to about 50 percent by weight of the powdered scent compound.

5. The powdered scent compound of claim 4, wherein the adhesive compound is selected from sodium carbonate, hydrogenated silica, and combinations thereof.

6. The powdered scent compound of claim 1, wherein the synthetic scent compound comprises one or more components selected from the group consisting essentially of: dioctyl adipate, ethyl laurate, benzyl benzoate, musk xylol, ethyl decanoate, p-cresol, p-cresyl phenylacetate, and phenyl acetic acid.

7. The powdered scent compound of claim 6, wherein the powdered scent compound further comprises about 1 percent or less by weight of the synthetic scent compound of an ingredient selected from the group consisting essentially of: benzyl alcohol, benzyl phenyl acetate, coumarin crystals, cuminic aldehyde, ethy-2-hexanol, ethylphenyl acetate, geranyl acetate, isovaleric acid, patchouli oil and combinations thereof.

8. The powdered scent compound of claim 1, wherein the powdered scent compound further comprises, about 1 percent or less by weight of the synthetic scent compound, an ingredient selected from the group consisting essentially of: benzyl alcohol, benzyl phenyl acetate, coumarin crystals, cuminic aldehyde, ethy-2-hexanol, ethylphenyl acetate, geranyl acetate, isovaleric acid, patchouli oil, and combinations thereof.

* * * * *